(12) United States Patent
Raghavan

(10) Patent No.: US 9,675,299 B2
(45) Date of Patent: Jun. 13, 2017

(54) MONITORING SYSTEM AND METHOD FOR VISUALLY PRESENTING HEALTH STATE OF A SUBJECT

(71) Applicant: General Electric Company, Schenectady, NY (US)

(72) Inventor: Jayaram Raghavan, Bangalore (IN)

(73) Assignee: General Electric Company, Schenectady, NY (US)

( * ) Notice: Subject to any disclaimer, the term of this patent is extended or adjusted under 35 U.S.C. 154(b) by 499 days.

(21) Appl. No.: 13/974,354

(22) Filed: Aug. 23, 2013

(65) Prior Publication Data

US 2014/0058216 A1    Feb. 27, 2014

(30) Foreign Application Priority Data

Aug. 24, 2012   (IN) .......................... 3491/CHE/2012

(51) Int. Cl.
*A61B 5/00* (2006.01)
*G06F 19/00* (2011.01)

(52) U.S. Cl.
CPC .......... *A61B 5/742* (2013.01); *G06F 19/3406* (2013.01); *G06F 19/345* (2013.01)

(58) Field of Classification Search
None
See application file for complete search history.

(56) References Cited

U.S. PATENT DOCUMENTS 5,674,190 A    10/1997  Kelly
5,978,691 A    11/1999  Mills
(Continued)

FOREIGN PATENT DOCUMENTS

CN    1158077 A    8/1997
CN    101642366 A    2/2010
(Continued)

OTHER PUBLICATIONS

Sensorworks (Aircraft Horizon Free, "https://play.google.com/store/apps/details?id=com.sensorworks.aircrafthorizon_free" Mar. 6, 2012).*

(Continued)

*Primary Examiner* — Xiao Wu
*Assistant Examiner* — Yu Chen
(74) *Attorney, Agent, or Firm* — GE Global Patent Operation; Marc A. Vivenzio

(57) ABSTRACT

The monitoring system for presenting a health state of a subject is disclosed. The monitoring system includes a processor for analyzing multiple health parameters associated with the subject. Based on this analysis, a health state indicator includes multiple gauges for visually presenting the health state of the subject. A gauge orients with respect to a gauge reference line based on the analyzed health parameters. In an embodiment, an interface element for visually presenting the health state of the subject in a monitoring system is disclosed. The interface element includes a health state indicator. The health state indicator includes multiple gauges, wherein one or more gauges orient with respect to one or more gauge reference lines based on analysis of the multiple health parameters to visually represent the health state of the subject. The health parameters are analyzed by the monitoring system.

11 Claims, 6 Drawing Sheets

(56) References Cited

U.S. PATENT DOCUMENTS

| | | | |
|---|---|---|---|
| 6,010,454 A * | 1/2000 | Arieff | G01N 21/62 |
| | | | 600/309 |
| 6,126,595 A | 10/2000 | Amano et al. | |
| 6,561,997 B1 | 5/2003 | Funke et al. | |
| 6,567,679 B1 | 5/2003 | Khuri et al. | |
| 7,081,091 B2 * | 7/2006 | Merrett | A61B 5/0205 |
| | | | 128/920 |
| 2003/0004066 A1 | 1/2003 | Iruvanti et al. | |
| 2003/0040665 A1 | 2/2003 | Khuri et al. | |
| 2008/0250341 A1 | 10/2008 | Dlugos et al. | |
| 2009/0046096 A1 * | 2/2009 | Rampersad | G06F 19/3406 |
| | | | 345/419 |
| 2011/0005114 A1 | 1/2011 | Snow | |
| 2011/0051141 A1 | 3/2011 | Mahmoodi et al. | |
| 2011/0230731 A1 | 9/2011 | Rantala et al. | |
| 2011/0237906 A1 * | 9/2011 | Kabakov | G06F 19/3406 |
| | | | 600/301 |
| 2013/0211214 A1 * | 8/2013 | Olsen | A61B 5/742 |
| | | | 600/316 |

FOREIGN PATENT DOCUMENTS

| | | |
|---|---|---|
| CN | 102197992 A | 9/2011 |
| CN | 2012017342 A1 | 2/2012 |
| WO | 2012067812 A1 | 5/2012 |

OTHER PUBLICATIONS

Unofficial English Translation of Chinese Office Action issued in connection with corresponding CN Application No. 201310372680.5 on Sep. 1, 2016.

* cited by examiner

MONITORING SYSTEM AND METHOD FOR VISUALLY PRESENTING HEALTH STATE OF A SUBJECT

BACKGROUND OF THE INVENTION

Human bodies manage a multitude of complex systems, and their interactions maintain balance of their health state. These interactions facilitate compensatory changes to support functioning of the physical and psychological activities of the human body. Several organs, like kidneys, livers, and brains, interact and function in a proper manner to maintain homeostasis. For example, livers are responsible for metabolizing toxic substances and maintain carbohydrate metabolism. Whereas kidneys are responsible for regulating blood water levels, re-absorption of substances into the blood, maintenance of salt and ion levels in the blood, regulation of blood pH, and excretion of urea and other wastes. So any imbalance in the homeostasis may lead to death or disease i.e., a condition known as homeostatic imbalance.

Frequent monitoring of the health state is essential to determine any homeostatic imbalance of the human body. Multiple monitoring devices are available that are used to perform various analysis such as arterial blood gas (ABG) analysis to determine different ABG parameters associated with the subject's body, and fluid balance analysis to determine any imbalance in functioning of different body fluids in the subject's body. The ABG analysis involves determining acid-base balance in the body and fluid balance analysis involves determining a balance between a fluid gain and fluid loss in the body. Different hormones in the human body, such as anti-diuretic hormones and aldosterone, may play the role of maintaining fluid balance. These monitoring devices may analyze various health parameters and present numerical values indicating the health parameter levels, such as acid-base balance and fluid balance. Then the numerical values need to be interpreted by a medical expert, such as a nurse, to determine a variation in the health state or homeostatic state of the subject. Interpretation of these numerical values to finalize the health state may be difficult, at times leading to medical treatment errors for the subject.

Thus there is a need for a monitoring system that is capable of visually presenting a health state of the subject to facilitate interpretation of the health state convenient for the medical expert.

BRIEF DESCRIPTION OF THE INVENTION

The above-mentioned shortcomings, disadvantages and problems are addressed herein which will be understood by reading and understanding the following specification.

As discussed in detail below, embodiments of the invention include a monitoring system for presenting a health state of a subject. The monitoring system includes a processor for analyzing multiple health parameters associated with the subject. Based on this analysis a health state indicator includes multiple gauges for visually presenting the health state of the subject. A gauge orients with respect to a gauge reference line based on the analyzed health parameters. In an embodiment, an interface element for visually presenting the health state of a subject in a monitoring system is disclosed. The interface element includes a health state indicator. The health state indicator includes multiple gauges, wherein one or more gauges orient with respect to one or more gauge reference lines based on analysis of the multiple health parameters to visually represent the health state of the subject. The health parameters are analyzed by the monitoring system.

In another embodiment, a method of presenting health state of a subject in a monitoring system is disclosed. The method involves initially analyzing multiple health parameters associated with the subject. A health state indicator including multiple gauges is provided. One or more gauges are oriented with respect to one or more gauge reference lines, based on an analysis of the health parameters performed in the monitoring system to visually present the health state of the subject.

DETAILED DESCRIPTION OF THE INVENTION

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the invention.

The monitoring system, including a processor for analyzing multiple health parameters associated with the subject, is disclosed. This analysis may be used by a health state indicator including multiple gauges. A gauge orients with respect to a gauge reference line based on the analyzed health parameters to visually present the health state of the subject. The health parameters may vary based on a type of analysis that is needed or performed. Different types of analysis may be performed, such as but not limited to arterial blood gas (ABG) analysis and fluid balance analysis. In ABG analysis, the health parameters that are monitored may include but are not limited to pH value, pCO2 level, HCO3 level, pO2 level, O2 Sat level, anion gap, delta ratio and SaO2 level. Whereas in the case of the fluid balance analysis, health parameters that need to be monitored may include but are not limited to sodium concentration in blood, water level in the body, glucose dialysate concentration, capillary refill time, blood pressure, skin elasticity, body weight, and urine output. Similarly it may be contemplated that other types of analysis may be performed and accordingly different health parameters may be analyzed to determine a health state of the subject.

Figure 1:
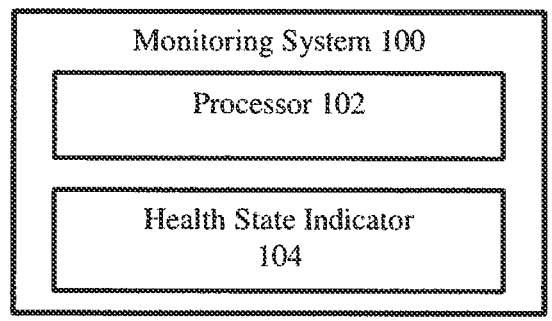
FIG. 1 is a schematic illustration of a monitoring system for presenting a health state of a subject in accordance with an embodiment.

FIG. 1 is a schematic illustration of a monitoring system 100 for presenting a health state of a subject in accordance with an embodiment. The subject may be any person whose health may need to be checked. In an embodiment the subject may be a patient present in the hospital whose health needs to be monitored continuously. The health state of the subject may be determined by performing different tests and analyses, such as but not limited to ABG analysis and fluid balance analysis. The monitoring system 100 may be used to conduct these tests and analyses on the subject. While performing analysis, multiple health parameters of the subject may be examined. A processor 102 of the monitoring system 100 receives and analyzes these health parameters to present the health state of the subject. The health state may be presented by a health state indicator 104 of the monitoring system 100. The health state indicator 104 includes multiple gauges that may function to present the subject's health state. In an embodiment, the health state indicator 104 may be an analog health state indicator. Alternatively the health state indicator 104 may be a graphical interface element.

Figure 2:
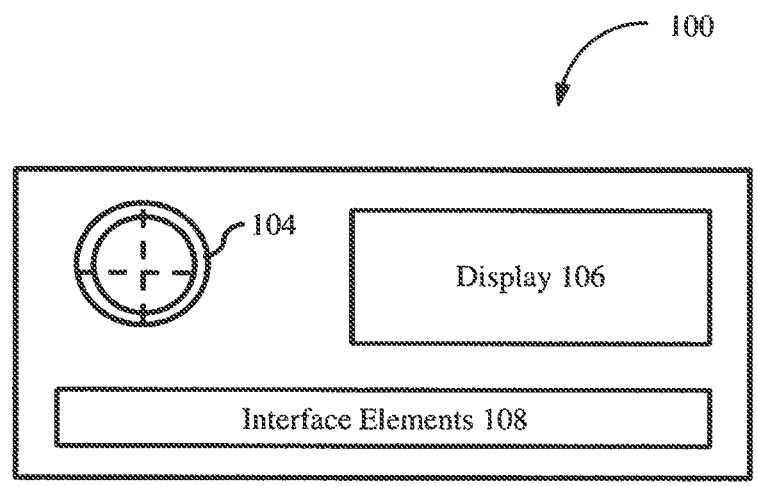
FIG. 2 is a schematic illustration of the monitoring system for presenting a health state of a subject.

Based on the analyzed health parameters, each gauge may orient with respect to a gauge reference line to present the health state of the subject visually. The gauge reference line represents a stable state associated with the health of the subject. So any deviation with respect to the gauge reference line indicates a change in the health state. The gauges may deviate with respect to their gauge reference lines in multiple axes such as X, Y and Z axes. This is explained in detail in conjunction with FIGS. 3-7. The visual presentation, provided by the health state indicator 104 as shown in FIG. 2 in accordance with an embodiment, helps a medical expert such as a doctor or a nurse to identify or interpret the health state of the subject accurately with less effort. In addition to the health state indicator 104, a display 106 may be provided in the monitoring system 100 to present various analysis results. The analysis results may include, for example but not limited to, different health parameter values and health parameter graphs. The monitoring system 100 may be operated by the medical expert using interface elements 108 provided. The interface elements 108 may include but are not limited to switches and graphical interface elements. In a scenario, the interface elements 108 may be part of a touch screen interface.

Figure 3:
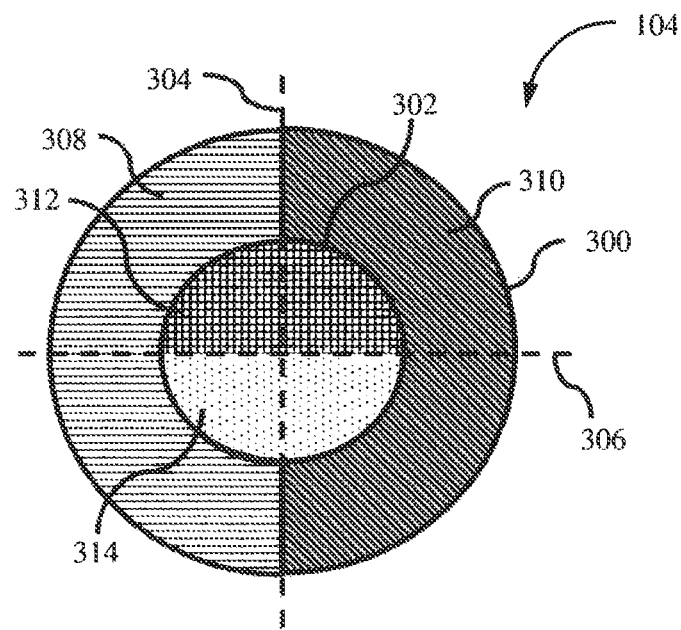
FIG. 3 is a schematic illustration of a health state indicator in the monitoring system in accordance with an exemplary embodiment.

FIG. 3 schematically illustrates the health state indicator 104 in accordance with an exemplary embodiment. The health state indicator 104 includes multiple gauges, for example a first gauge 300 and a second gauge 302. During operation the first gauge 300 and the second gauge 302 orient with respect to a gauge reference line 304 and a gauge reference line 306 respectively. The gauge reference line 306 and the gauge reference line 304 may be associated with X and Y axes respectively. Further in another embodiment, the first gauge 300 and the second gauge 302 may also be configured to orient with respect to a Z axis (not shown in FIG. 3) in a three dimensional space. In this instance the health state indicator 104 may have a three dimensional structure and thus the first gauge 300 may be a disc and the second gauge 302 may be a spherical element capable of rotating in the Z axis. Another gauge reference line may be present to represent the Z axis. The health state indicator 104 and their gauges are described as capable of orienting with respect to X and Y axes for sake of convenience of description according to an embodiment. However it may be contemplated in other embodiments that the health state indicator 104 and their gauges may be configured in any other manner and that logical, mechanical, electrical and other changes may be made without departing from the scope of the embodiments described herein.

The health state indicator 104 may present orientation of the first gauge 300 and the second gauge 302 with respect to the gauge reference line 304 and the gauge reference line 306 over a period of time or different instances in an embodiment. Thus the health state indicator 104 shows the variation in orientation of these gauges in an animated configuration or a slow animated configuration presenting a change or trend in change of the health state of the subject. The trend in change of the health state may be deduced by the medical expert to determine if there are any alarming variations in the health state and therefore the subject requires immediate medical attention.

Now considering an example of ABG analysis, the first gauge 300 may be an organ imbalance gauge that indicates a state associated with an organ of the subject. Whereas the second gauge 302 may be a health parameter gauge indicating the status of a health parameter. In an embodiment, the first gauge 300 and the second gauge 302 may also present numerical values associated with the organ imbalance and the health parameters. The numerical values may be displayed as a meter on these gauges and one or more needles for indicating the numerical values in the meter may be provided. In an embodiment the meter and needles may be displayed on the health state indicator when a user (such as the medical expert) activates them using any menu option or interface elements (for example the interface elements 108) present in the monitoring system. The meter and needles may be overlaid on the gauges and the user may activate or deactivate them based on their discretion. In another embodiment the health state indicator 104 may be selectively activated and deactivated by the user. The health state indicator 104 may be activated and deactivated using an interface element in a display such as the display 106 of the monitoring system 100. When activated the health state indicator 104 may be displayed in the display. The health state indicator 104 may be overlaid on the analysis results such as the health parameter values and the graphs presented in the display. Now when deactivated the health state indicator 104 is removed from the display. In an exemplary embodiment the health state indicator 104 may be presented as a screen saver in the display. The medical expert or any care giver may be able to view the health state indicator 104 and deduce the health state of the subject at a glance even from a distance. Such a feature of the health state indicator 104 is less traumatic for the subject and care givers of the subject. It may be envisaged that the health state indicator 104 may be presented in the display in any other configuration convenient for deducing the health state of the subject without departing from the scope of this description.

The health state indicator 104 is hereinafter explained in detail with respect to FIGS. 3-7 considering the example of ABG analysis, however it may be contemplated that the health state indicator 104 may include multiple gauges that represent various other health parameters and health status of different organs of the subject based on a type of test and analysis performed on the subject.

Referring back to the first gauge 300, this gauge includes a first indicating element 308 and a second indicating element 310. These indicating elements may be associated with different organs of the subject. For example the first indicating element 308 may be associated with a respiratory system and the second indicating element 310 may be associated with a metabolic system. In an embodiment, the first indicating element 308 and the second indicating element 310 may be assigned different color codes. For example the first indicating element 308 and the second indicating element 310 may be assigned a blue color and a brown color respectively. These color codes may be provided based on an organ to which the color is associated. However it may be contemplated that the indicating elements in the first gauge 300 may be presented in any other forms in order to conveniently present the imbalance of the subject's organ even from a distance. The first gauge 300 rotates with respect to the gauge reference line 304 to indicate an imbalance in an organ of the subject. So if the first gauge 300 does not deviate from the gauge reference line 304 as illustrated in FIG. 3 then it indicates that the organs are functioning in a balanced manner.

The second gauge 302 includes a first indicator 312 and a second indicator 314. The second gauge 302 may move with respect to the gauge reference line 306 to indicate a variation in a health parameter, such as pH level. Moreover in an embodiment, the second gauge 302 may orient or move in other axes to represent variations in the health parameters. Thus if the second gauge 302 does not deviate from the gauge reference line 306 then it indicates that the health parameter, for example pH level in the subject's blood, is normal. In an embodiment the first indicator 312 and the second indicator 314 may be assigned different color codes. For example, the first indicator 312 and the second indicator 314 may be assigned a blue color and a brown color respectively. However these indicators may be differentiated in any other convenient form so that they are visible from a distance. In an embodiment the first gauge 300 and the second gauge 302 may also include one or more meters along with needles to indicate health parameter values associated with the imbalance of the organ and the health parameter. Nevertheless it may be envisaged that the health parameter values may be displayed on the second gauge 302 using any other techniques.

Figure 4:
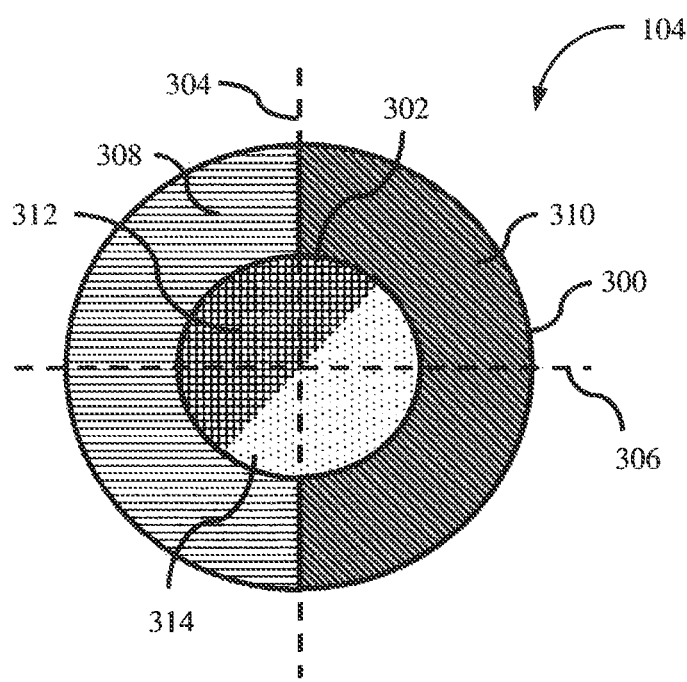
FIG. 4 is a schematic illustration of the health state indicator indicating a health state of the subject i.e., uncompensated respiratory acidosis in accordance with an exemplary embodiment.

Based on the analyzed health parameters the first gauge 300 and the second gauge 302 may rotate with respect to their respective gauge reference lines to present the health state of the subject. FIG. 4 illustrates the health state indicator 104 having the first gauge 300 and the second gauge 302 changing their orientation to represent a health state such as uncompensated respiratory acidosis in accordance with an exemplary embodiment. As shown in FIG. 4 the second gauge 302 rotates in a left direction with respect to the gauge reference line 306, then the first indicator 312 moves beyond the gauge reference line 306 to indicate an acidic pH.

Now as illustrated, the first gauge 300 does not rotate with respect to the gauge reference line 304. Moreover the first indicating element 308 is positioned at the left side proximal to the first indicator 312 indicating imbalance in the respiratory system. As the second gauge 302 does not rotate or move in a horizontal axis it shows that there is no compensation by the metabolic system. More specifically the first gauge 300 does not move away from a coinciding point of the gauge reference lines. The orientation of the first gauge 300 and the second gauge 302 enable the medical expert to identify the health state of the subject as uncompensated respiratory acidosis.

Figure 5:
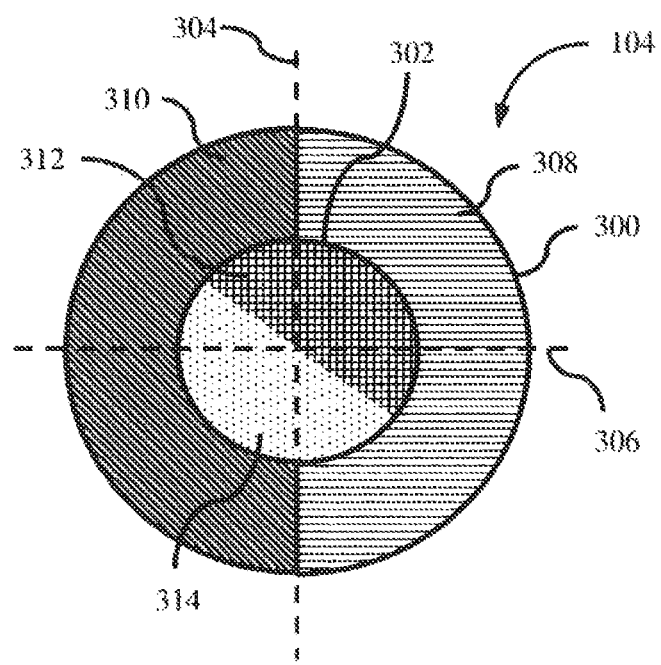
FIG. 5 is a schematic illustration of the health state indicator indicating a health state of the subject i.e., uncompensated respiratory alkalosis in accordance with an exemplary embodiment.

In another instance the first gauge 300 and the second gauge 302 may rotate with respect to the gauge reference line 304 and the gauge reference line 306 as schematically illustrated in FIG. 5 in accordance with an exemplary embodiment. As the second gauge 302 rotates in a right direction, the second indicator 314 moves beyond the gauge reference line 306. This represents a shift towards an alkaline pH in the subject's blood.

The first gauge 300 rotates in the right direction to move beyond the gauge reference line 304 so as to align the first indicating element 308 in an opposite position as opposed to its stable position as shown in FIG. 3. This represents that the respiratory system is in an imbalanced state. In an embodiment wherein the first indicating element 308 is provided a blue color, the medical expert can conveniently visualize based on the color and recognize that the imbalance is in the respiratory system. Now when the second gauge 302 does not rotate with respect to the horizontal axis, then the indication is that there is no attempt for compensation by the metabolic system. Viewing the orientations of the gauges the medical expert can conveniently identify the health state of the subject as uncompensated respiratory alkalosis. Moreover this visual presentation also enables the medical expert to reduce the time for determining the current health state of the subject. Thus proper medical treatment can be provided to the subject in a timely manner to bring the health state to a stable condition.

Figure 6:
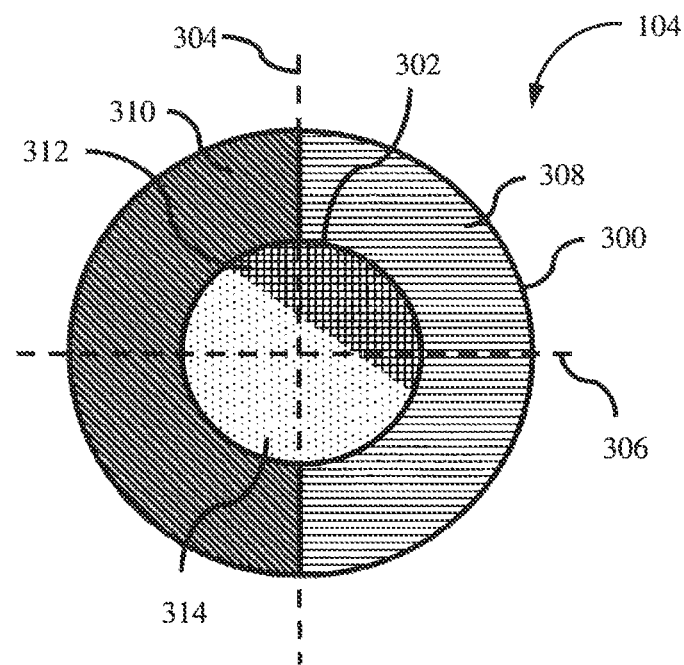
FIG. 6 is a schematic illustration of the health state indicator indicating a health state of the subject i.e., compensated respiratory alkalosis in accordance with an exemplary embodiment.

FIG. 6 schematically illustrates the health state indicator 104 to indicate another health state of the subject in accordance with an exemplary embodiment. In this scenario, the second gauge 302 rotates in a right direction allowing the second indicator 314 to move beyond the gauge reference line 306. The orientation of the second gauge 302 represents a shift towards an alkaline pH in the subject's blood. The first gauge 300 rotates in the right direction as compared to the stable position as shown in FIG. 3. More specifically the first gauge 300 rotates to orient the first indicating element 308 at the right side of the gauge reference line 304 indicating that imbalance is associated with the respiratory system. The second gauge 302 may rotate with respect to the horizontal axis such that a center point of the gauge reference lines (i.e. the gauge reference line 304 and the gauge reference line 306) falls within the second indicator 314. This represents that the metabolic system provides compensation for the pH variation. However the pH compensation is not enough; as a result the pH level is indicated as abnormal by the orientation of the second indicator 314 due to the partial compensation provided by the metabolic system. Thus the orientation of the first gauge 300 and the second gauge 302 enables the medical expert to deduce the health state of the subject as partially compensated respiratory alkalosis.

Figure 7:
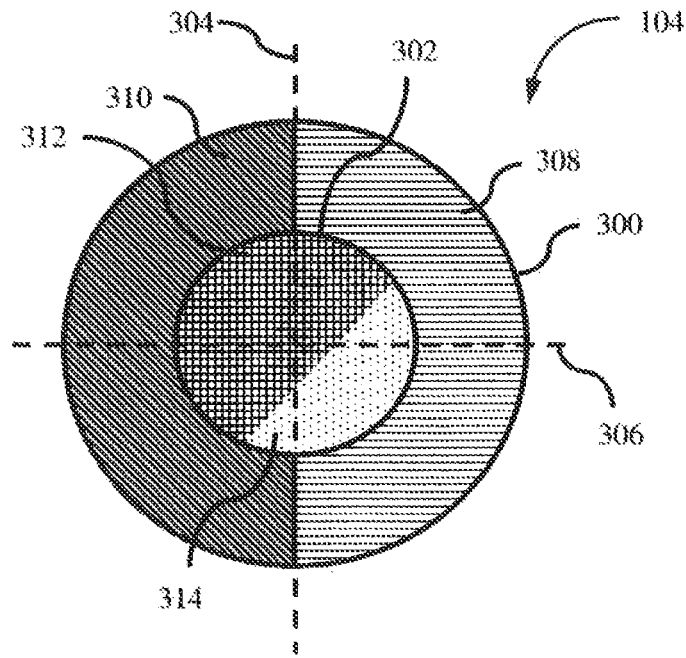
FIG. 7 is a schematic illustration of the health state indicator indicating a health state of the subject i.e., compensated metabolic acidosis in accordance with an exemplary embodiment.

In another instance the health state of the subject may be indicated as partially compensated metabolic acidosis by the health state indicator 104. FIG. 7 schematically illustrates the health state indicator 104 wherein the second gauge 302 rotates in a left direction thereby allowing the first indicator 312 to move beyond the gauge reference line 306 in accordance with an exemplary embodiment. This represents a shift towards an acidic pH in the subject's blood. As illustrated the first gauge 300 rotates to the right direction compared to the stable position as shown in FIG. 3. More specifically the first gauge 300 rotates to orient the second indicating element 310 at the left side of the gauge reference line 304 showing that imbalance is associated with the metabolic system. Further the second gauge 302 moves with respect to the horizontal axis such that the center point of the gauge reference lines is aligned to the first indicator 312 indicating that the respiratory system is providing compensation for the acidic pH imbalance. However this compensation may be partial in nature due to the imbalance in the acidic pH by the second gauge 302. After viewing these gauges the medical expert may deduce the health state of the subject as partially compensated metabolic acidosis.

Figure 8:
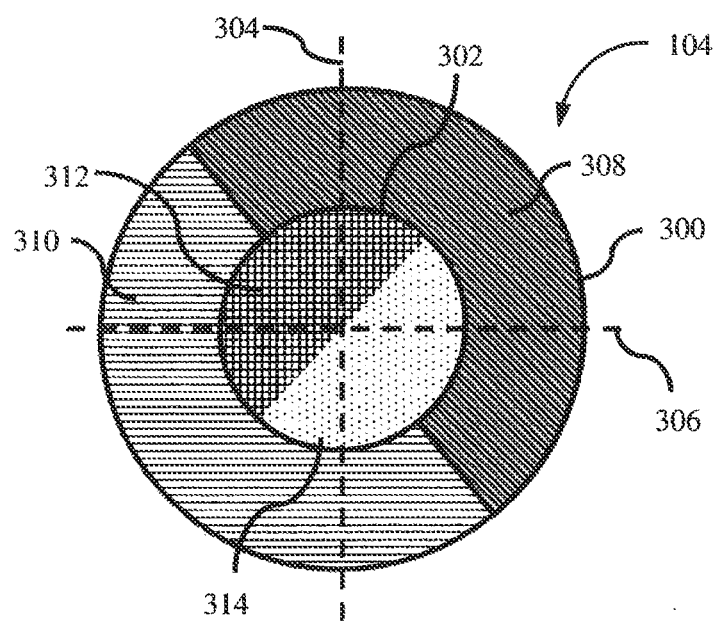
FIG. 8 is a schematic illustration of the health state indicator indicating a health state of the subject i.e., mixed respiratory and metabolic acidosis state in accordance with an exemplary embodiment.

FIG. 8 schematically illustrates the health state indicator 104 including the first gauge 300 and the second gauge 302 capable of orienting with respect to the gauge reference line 304 and the gauge reference line 306 to indicate another imbalanced health state of the subject in accordance of an exemplary embodiment. As shown in FIG. 8, the second gauge 302 rotates in the left direction whereby the first indicator 312 moves beyond by the gauge reference line 306 to indicate an acidic pH imbalance. The second gauge 302 does not rotate with respect to the horizontal axis. Further the first gauge 300 rotates with respect to the gauge reference line 304 in the left direction deviating from the stable position as shown in FIG. 3. When the first gauge 300 rotates a portion of the first indicating element 308 and the second indicating element 310 moves beyond the gauge reference line 304. The orientation of the first indicating element 308 and the second indicating element 310 indicates that both the respiratory and the metabolic systems are in an imbalanced state. This mixed respiratory and metabolic acidosis state can be determined by the medical expert by viewing the health state indicator 104 conveniently. Such a state may be found commonly in critically ill patients present in the hospital and thus proper medication can be provided to the patients for regaining the balanced state.

Figure 9:
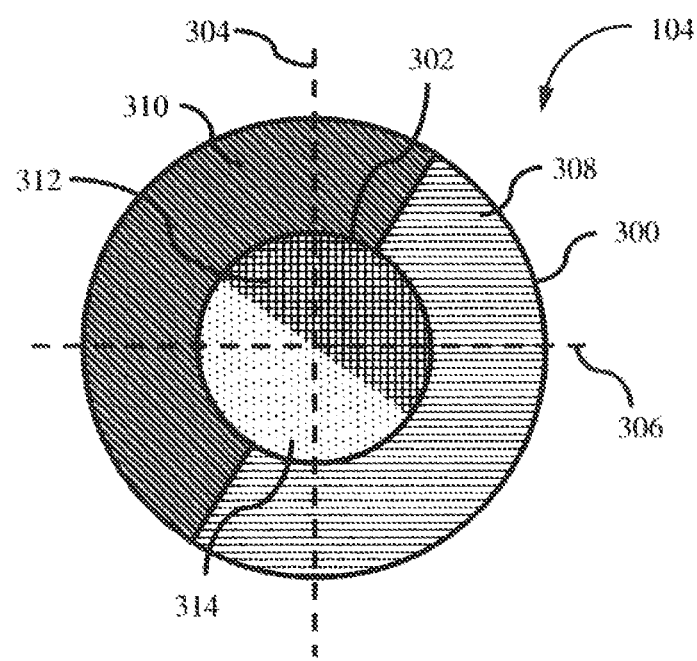
FIG. 9 is a schematic illustration of the health state indicator indicating a health state of the subject i.e., mixed respiratory and metabolic alkalosis state in accordance with an exemplary embodiment.

In another instance the health state of the subject may be a mixed respiratory and metabolic alkalosis indicated by the health state indicator 104 as shown in FIG. 9 in accordance with an embodiment. In the health state indicator 104, the second gauge 302 rotates in a right direction whereby the first indicator 312 moves beyond the gauge reference line 306 to indicate an alkaline pH imbalance. The second gauge 302 does not rotate with respect to the horizontal axis. Further, the first gauge 300 rotates with respect to the gauge reference line 304 in the right direction deviating from the stable position as shown in FIG. 3. When the first gauge 300 rotates, a portion of the first indicating element 308 and the second indicating element 310 moves beyond the gauge reference line 304. The orientation of the first indicating element 308 and the second indicating element 310 indicates that both the respiratory and the metabolic systems are in imbalance state. This mixed respiratory and metabolic alkalosis state can be determined by the medical expert by viewing the health state indicator 104 conveniently. Such a state may be found commonly in critically ill patients present in the hospital and thus proper medication can be provided to the patients for regaining the balanced state.

Now it may be envisaged that the health state indicator 104 and their gauges such as the first gauge 300 and the second gauge 302 may be configured to present the health state of the subject based on analysis results of various other tests such as but not limited to fluid balance analysis even though the health state indicator 104 is explained to show the health state based on the ABG analysis in FIGS. 1-9. The health state indicator such as the health state indicator 104 may include more than two gauges, and gauges having any other configurations based on the tests and analysis may be presented without deviating from the scope of this description.

Figure 10:
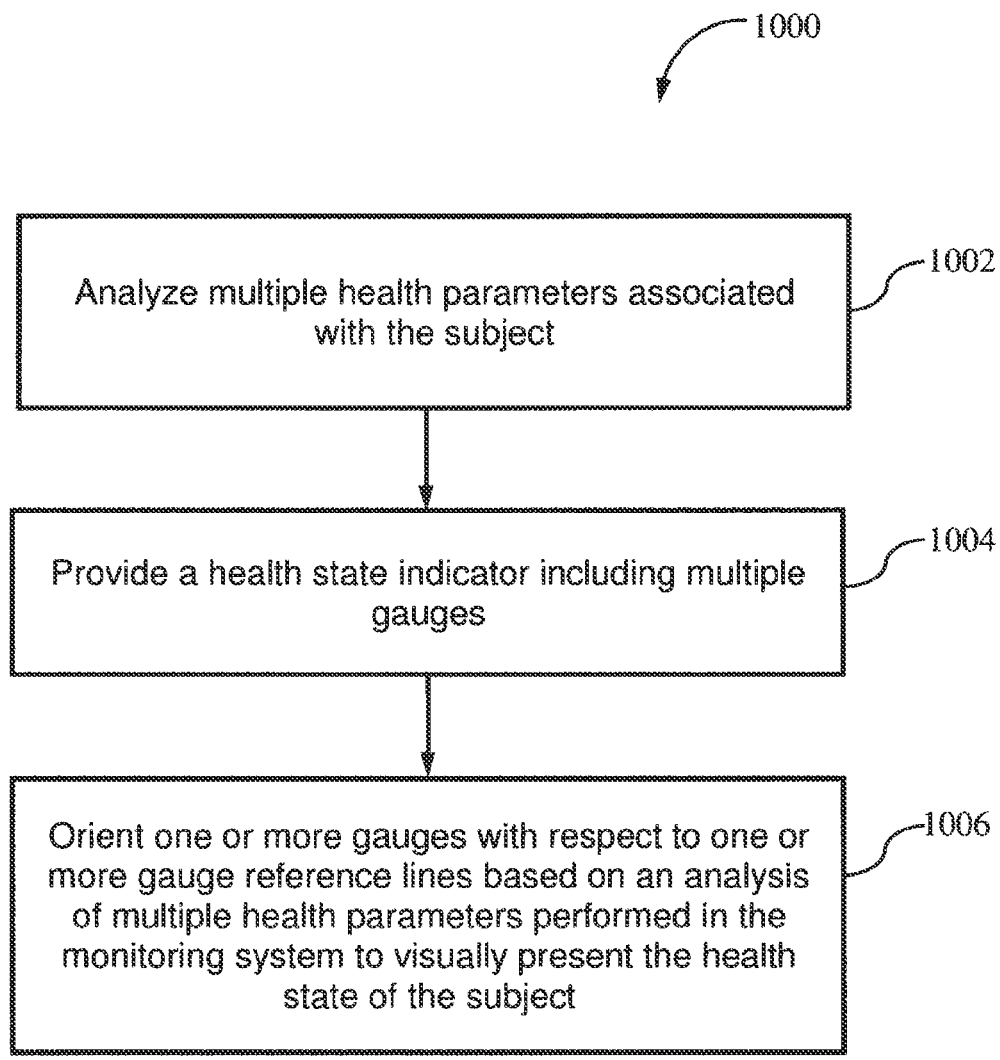
FIG. 10 is a flow chart of a method for presenting health state of a subject in a monitoring system in accordance with an embodiment.

FIG. 10 is a flow chart of a method 1000 for presenting a health state of a subject in a monitoring system in accordance with an embodiment. The subject may be any person whose health may need to be checked. The health state of the subject may be determined by performing different tests and analysis such as but not limited to, ABG analysis and fluid balance analysis. In an embodiment, the monitoring system may be used to conduct these tests and analyses on the subject. While performing the analyses, multiple health parameters of the subject may be examined. These health parameters may be received and analyzed at step 1002 to present the health state of the subject. The health state may be presented by a health state indicator provided in the monitoring system at step 1004. For example the health state indicator 104 of the monitoring system 100 may visually present the health state of the subject. The health state indicator includes multiple gauges that may function to present the subject's health state. In an embodiment, the health state indicator may be an analog health state indicator. Alternatively the health state indicator may be a graphical interface element.

Based on the analyzed health parameters, each gauge may orient with respect to a gauge reference line to visually present the health state of the subject at step 1006. The gauge reference line represents a stable state associated with the health of the subject. So any deviation with respect to the gauge reference line indicates a change in the health state. The gauges may orient with respect to their gauge reference line in multiple axes such as X, Y and Z axes. The visual presentation provided by the health state indicator helps a medical expert, such as a doctor or a nurse, to identify or interpret the health state of the subject accurate manner with less effort. Further in another embodiment, the gauges of the health state indicator may also be configured to orient with respect to a Z axis in a three dimensional space. In this instance the health state indicator may have a three dimensional structure and thus a first gauge may be a disc and the second gauge may be a sphere capable of rotating in the Z axis. Another gauge reference line may be present to represent the Z axis. The health state indicator and their gauges are described as capable of orienting with respect to X and Y axes for sake of convenience of description according to an embodiment. However it may be contemplated that in other embodiments the health state indicator and their gauges may have other configurations and that logical, mechanical, electrical and other changes may be made without departing from the scope of the embodiments described herein.

For instance a health state indicator may include multiple gauges, for example a first gauge and a second gauge. During operation the first gauge and the second gauge may orient with respect to a first gauge reference line and a second gauge reference line respectively. Now considering an example of ABG analysis, the first gauge may be an organ imbalance gauge that indicates a state associated with an organ of the subject. The first gauge may include a first indicating element and a second indicating element. These indicating elements may be associated with different organs of the subject. For example the first indicating element may be associated with a respiratory system and the second indicating element may be associated with a metabolic system. In an embodiment the first indicating element and the second indicating element may be assigned different color codes. These color codes may be provided based on an organ to which the color is associated. The first gauge may rotate with respect to the first gauge reference line to indicate an imbalance in an organ of the subject. So if the first gauge is oriented with respect to the first gauge reference line such as the gauge reference line 304 as illustrated in FIG. 3 then it indicates that the organs are functioning in a balanced manner.

The second gauge may be a health parameter gauge indicating the status of a health parameter. The second gauge includes a first indicator and a second indicator. The second gauge rotates with respect to the second gauge reference line such as the gauge reference line 306 to indicate a variation in a health parameter such as, pH level. Moreover in an embodiment the second gauge may orient or move in other axes to represent variations in the health parameters. In an embodiment the first indicator and the second indicator may be assigned different color codes. In an embodiment the first gauge and the second gauge may also include meter values that indicates values associated with the imbalance of the organ and the health parameter. Based on the analyzed health parameters the first gauge and the second gauge may rotate with respect to their respective gauge reference lines to present the health state of the subject. The medical expert may view the orientation of these gauges to determine the health state of the subject with ease.

The method 1000 can be performed using a processor or any other processing device. The method steps can be implemented using coded instructions (e.g., computer readable instructions) stored on a tangible computer readable medium. The tangible computer readable medium may be a flash memory, a read-only memory (ROM), a random access memory (RAM), any other computer readable storage medium, or any storage media. Although the method for presenting health state of a subject in a monitoring system is explained with reference to the flow chart of FIG. 10, other methods of implementing the method can be employed. For example, the order of execution of each method steps may be changed, and/or some of the method steps described may be changed, eliminated, divide or combined. Further the method steps may be sequentially or simultaneously executed for presenting health state of a subject in a monitoring system.

This written description uses examples to disclose the invention, including the best mode, and also to enable any person skilled in the art to practice the invention, including making and using any computing system or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A health state indicator comprising:
at least a first gauge and a second gauge, the first gauge configured to display at least a first measured physiological parameter of a subject and the second gauge configured to display at least a second measured physiological parameter of the subject,
the first gauge comprising a disc shaped indicating element configured to rotate with respect to a y-axis reference of the health state indicator to indicate an imbalance of the at least first measured physiological parameter, the disc shaped indicating element comprising a gauge reference line that is aligned with the y-axis reference line of the health state indicator to indicate a stable health state of the subject;
the second gauge comprising a sphere shaped indicator element disposed within an interior portion of the disc shaped element of the first gauge, the sphere shaped indicator element of the second gauge configured to rotate with respect to an x-axis and a z-axis reference of the health state indictor independently of the disc shaped indicating element of the first gauge, the second gauge comprising gauge reference lines aligned with the x-axis reference and the z-axis reference of the health state indicator to indicate the stable health state of the subject, and wherein the sphere shaped indicator of the second gauge rotates with respect to the x-axis and the z-axis to indicate an imbalance of the at least second measured physiological parameter;
the first gauge and the second gauge configured to display a diagnostic representation of the at least first measured physiological parameter and the at least second measured physiological parameter.

2. The health state indicator of claim 1, wherein the first indicating element and the second indicating element of the first gauge is associated with a unique color code.

3. The health state indicator of claim 1, wherein the health state indicator comprises at least one of an analog gauge and a digital gauge.

4. The health state indicator of claim 1, wherein quantitative data from a selected gauge from the at first gauge and the at least second gauge is one or more of overlaid or displayed alongside the health indicator.

5. The health state indicator of claim 1, wherein the at least first gauge and the at least second gauge are at least one of digital, analogue, and a combination of digital and analogue.

6. The health state indicator of claim 1 wherein a plurality of health state indicators are configured to form a health state monitoring system.

7. The health state indicator of claim 1, wherein the disc shaped indicating element of the first gauge comprises a first indicating portion and a second indicating portion, and wherein a reference line between the first indicating portion and the second indicating portion aligns with the y-axis reference of the health state indicator to indicate the stable health state of the subject.

8. The health state indicator of claim 7, wherein the sphere shaped indicating element of the second gauge comprises a first indicator portion and a second indicator portion and wherein a reference line between the first indicator portion and the second indicator portion aligns with the x-axis reference of the health state indicator to indicate the stable health state of the subject.

9. A method of presenting a health state of a subject on a display of a monitoring system, the method comprising:
providing at least a first gauge and a second gauge on the display of the monitoring system, a sphere shaped indicator of the second gauge being disposed within an interior portion of a disc shaped element of the first gauge;

aligning an indicating element of the first gauge with a y-axis reference of the display in a first state of the first gauge;

aligning indicator elements of the second gauge with an x-axis reference and a z-axis reference of the display in a first state of the second gauge;

providing the first gauge a first physiological parameter of a subject and a second physiological parameter of the subject to the second gauge;

causing the indicating element of the first gauge to deviate from the y-axis reference to indicate a change of the first physiological parameter; and causing the indicating elements of the second gauge to deviate from the x-axis and z-axis reference to indicate a change of the second physiological parameter.

10. The method of claim 9, wherein the first gauge and the second gauge form a health indicator, wherein the indicating element of the first gauge is associated with a first color code and the indicator element of the second gauge is associated with a second color code.

11. The method of claim 9, wherein quantitative data from a selected gauge from the at least first gauge and the at least second gauge is overlaid and/or displayed alongside at least one of the gauges and/or the health indicator.

* * * * *